United States Patent
Von Hagen et al.

(10) Patent No.: US 10,619,131 B2
(45) Date of Patent: *Apr. 14, 2020

(54) CELL CULTURE MEDIA

(71) Applicant: Merck Patent GmbH, Darmstadt (DE)

(72) Inventors: Joerg Von Hagen, Pfungstadt (DE); Marcel Andre Breuning, Frankfurt am Main (DE); Christian Jasper, Seligenstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/952,874

(22) Filed: Apr. 13, 2018

(65) Prior Publication Data

US 2018/0230422 A1    Aug. 16, 2018

Related U.S. Application Data

(63) Continuation of application No. 14/442,821, filed as application No. PCT/EP2013/003441 on Nov. 14, 2013, now Pat. No. 10,030,225.

(30) Foreign Application Priority Data

Nov. 14, 2012 (EP) .................... 12007711

(51) Int. Cl.
  *C12N 5/00* (2006.01)
  *C12N 1/20* (2006.01)
  *C07F 9/09* (2006.01)

(52) U.S. Cl.
  CPC .............. *C12N 5/0018* (2013.01); *C07F 9/09* (2013.01); *C12N 1/20* (2013.01); *C12N 5/0025* (2013.01); *C12N 2500/32* (2013.01); *C12N 2500/33* (2013.01)

(58) Field of Classification Search
  CPC ......... C07F 9/09; C12N 1/20; C12N 2500/32; C12N 2500/33; C12N 5/0018; C12N 5/0025
  See application file for complete search history.

(56) References Cited

U.S. PATENT DOCUMENTS

| | | | |
|---|---|---|---|
| 5,824,552 A | 10/1998 | Takazawa | |
| 8,143,223 B2 | 3/2012 | Dittmann et al. | |
| 10,030,225 B2 * | 7/2018 | Von Hagen | C12N 5/0018 |
| 2004/0142908 A1 | 7/2004 | Dittmann et al. | |
| 2005/0038258 A1 | 2/2005 | Koike et al. | |
| 2007/0286887 A1 | 12/2007 | Kaminoyama et al. | |
| 2010/0233765 A1 | 9/2010 | Nonaka | |

FOREIGN PATENT DOCUMENTS

| | | |
|---|---|---|
| JP | 62051117 B2 | 10/1987 |
| JP | 2006-515502 A | 6/2006 |
| JP | 2010-503397 A | 2/2010 |
| JP | 2011-512844 A | 4/2011 |
| WO | 02/081028 A2 | 10/2002 |
| WO | 03053932 A1 | 7/2003 |
| WO | 03064630 A2 | 8/2003 |
| WO | 2006/062238 A1 | 6/2006 |
| WO | 2008033517 A2 | 3/2008 |
| WO | 2009111066 A1 | 9/2009 |
| WO | 2010/115838 A1 | 10/2010 |
| WO | WO-2010115838 A1 * | 10/2010 ............ C12P 17/188 |

OTHER PUBLICATIONS

Macine translation of JP 62051117 (published 1987) downloaded from ProQuest on Nov. 26, 2017 (Year: 1987).*
Suzuki et al. Agric. Biol. Chem. (1997) 44(8): 1995-1997 (Year: 1997).*
International Search Report dated Mar. 19, 2014 issued in corresponding PCT/EP2013/003441 application (pp. 1-6).
K.H. Dittmann et al., "O-phospho-L-tyrosine Protects TP53 Wild-Type Cells Against Ionizing Radiation", International Journal of Cancer, vol. 96 Suppl. (Jan. 1, 2001) pp. 1-6.
S. Mishra et al., "Association of Inhibition of Cell Growth by O-Phospho-L-Tyrosine with Decreased Tyrosine Phosphorylation", Cancer Letters, vol. 102 (Jan. 1, 1996) pp. 65-71.
R.H.A. Plimmer, "Esters of Phosphoric Acid—Phosphoryl Hydroxyamino-Acids", Retrieved from the Internet: URL: http://www.biochemj.org/bj/035/0461/0350461.pdf (Jan. 1, 1941) pp. 461-469.
T. Nakatani et al., "Enhancement of Thioredoxin/Glutaredoxin-Mediated L-Cysteine Synthesis from S-Sulfocysteine Increases L-Cysteine Production in *Escherichia coli*", Microbial Cell Factories, vol. 11, No. 1 (May 18, 2012) pp. 1-9.
A. Fasth et al., "Protective Effect of Thiosulfate and Metabolic Thiosulfate Precursors Against Toxicity of Nitrogen Mustard (HN2)", Biochemical Pharmacology, vol. 22, No. 11 (Jun. 1, 1973) pp. 1337-1351.
Klayman et al. J. Med. Chern. (1969) 12: 510-512 (Year: 1969).
Xie et al. Biotech. Bioengineer. (1994) 43: 1175-89.
Fujisawa Agric. Biol. Chem. (1982) 4696): 1519-1523.

* cited by examiner

*Primary Examiner* — Susan M Hanley
(74) *Attorney, Agent, or Firm* — Millen White Zelano & Branigan (57) ABSTRACT

The present invention relates to cell culture media comprising inorganic ester derivatives of tyrosine and/or cysteine. The poor solubility of tyrosine and the often non-sufficient stability of cysteine in cell culture media is overcome by substituting them with an inorganic ester derivative, e.g. with a phosphorylated derivative.

10 Claims, 8 Drawing Sheets

CELL CULTURE MEDIA

The present invention relates to cell culture media comprising inorganic ester derivatives of tyrosine and/or cysteine. The poor solubility of tyrosine and the often non-sufficient stability of cysteine in cell culture media is overcome by substituting them with an inorganic ester derivative, e.g. with a phosphorylated derivative.

Cell culture media support and maintain the growth of cells in an artificial environment.

Depending on the type of organism whose growth shall be supported, the cell culture media comprise a complex mixture of components, sometimes more than one hundred different components.

The cell culture media required for the propagation of mammalian, insect or plant cells are typically much more complex than the media to support the growth of bacteria and yeasts.

The first cell culture media that were developed consisted of undefined components, such as plasma, serum, embryo extracts, or other non-defined biological extracts or peptones. A major advance was thus made with the development of chemically defined media. Chemically defined media often comprise but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from said cells.

Most biopharmaceutical production platforms are based on fed-batch cell culture protocols. The aim typically is to develop high-titer cell culture processes to meet increasing market demands and reduce manufacturing costs. Beside the use of high-performing recombinant cell lines, improvements in cell culture media and process parameters are required to realize the maximum production potentials In a fed-batch process, a basal medium supports initial growth and production, and a feed medium prevents depletion of nutrients and sustains the production phase. The media are chosen to accommodate the distinct metabolic requirements during different production phases. Process parameter settings—including feeding strategy and control parameters—define the chemical and physical environments suitable for cell growth and protein production.

Optimization of the feed medium is major aspect in the optimization of a fed-batch process.

Mostly the feed medium is highly concentrated to avoid dilution of the bioreactor. The controlled addition of the nutrient directly affects the growth rate of the culture.

A limiting factor for the preparation of cell culture media from dry powder is the poor solubility or stability of some components, especially the poor solubility or stability of the amino acids L-tyrosine and L-cysteine. For L-tyrosine, the poor solubility is the main problem, whereby for L-cysteine, stability problems dominate.

Consequently it would be favourable to find a way to improve the solubility and/or stability of L-tyrosine and L-cysteine.

It has been found that inorganic ester derivatives of L-tyrosine and L-Cysteine have an improved solubility and/or stability and can be used in cell culture media instead of L-tyrosine and L-cysteine respectively without any negative effect and sometimes even positive effect on the cell growth.

It has further been found that such inorganic ester derivatives are especially suitable for preparing feed solutions that have a pH of not more than pH 8.5 and that have high concentrations of tyrosine and cysteine which are in a form suitable as a nutrient for cells.

The present invention is therefore directed to cell culture media comprising at least one inorganic ester derivative of tyrosine and/or cysteine.

In a preferred embodiment, the inorganic ester derivative is a sulphate ester derivative or a phosphate ester derivative.

In a preferred embodiment the cell culture medium comprises one or more of the components of formula I and/or II:

In a preferred embodiment, the inorganic ester derivative of tyrosine is (S)-2-Amino-3-(4-phosphonooxy-phenyl)-propionic acid or salts thereof.

In another preferred embodiment, the derivative of cysteine is (S)-2-amino-3-sulfosulfanylpropanoic acid or salts thereof.

In a preferred embodiment the phosphorylated derivative of tyrosine is (S)-2-Amino-3-(4-phosphonooxy-phenyl)-propionic acid di-sodium salt.

In a preferred embodiment the sulfonated derivative of cysteine is (S)-2-amino-3-sulfosulfanylpropanoic acid sodium salt.

In a preferred embodiment, the cell culture medium is a dry powder medium.

In another preferred embodiment, the cell culture medium is a feed medium.

In another preferred embodiment the cell culture medium is a liquid medium having a pH of 8.5 or less and comprising at least one inorganic ester derivative of tyrosine and/or cysteine in a concentration between 5 and 40 mmol/l, preferably between 10 and 30 mmol/l.

In a preferred embodiment the pH of the liquid medium is between 6.5 and 8.5, most preferred between 6.8 and 7.8.

In one embodiment, the cell culture medium comprises at least one or more saccharide components, one or more amino acids, one or more vitamins or vitamin precursors, one or more salts, one or more buffer components, one or more co-factors and one or more nucleic acid components.

The present invention is further directed to a method for producing a cell culture medium according to the present invention by a) mixing one or more inorganic ester derivatives of L-tyrosine and/or L-cysteine with the other components of the cell culture medium
b) subjecting the mixture of step a) to milling In a preferred embodiment step b) is performed in a pin mill, fitz mill or a jet mill.

In another preferred embodiment, the mixture from step a) is cooled to a temperature below 0° C. prior to milling.

The present invention is further directed to the di-sodium salt, the di-potassium salt, the mono-potassium salt, the 2:1 calcium salt and the magnesium salts of (S)-2-Amino-3-(4-phosphonooxy-phenyl)-propionic acid.

The present invention is further directed to a process for culturing cells by
a) providing a bioreactor
b) mixing the cells to be cultured with a cell culture medium according to the present invention.
c) incubating the mixture of step b).

The present invention is also directed to a fed batch process for culturing cells in a bioreactor by
Filling into a bioreactor cells and an aqueous cell culture medium
Incubating the cells in the bioreactor
Continuously over whole time of the incubation of the cells in the bioreactor or once or several times within said incubation time adding a cell culture medium, which is in this case a feed medium, to the bioreactor whereby the feed medium has a pH of less than pH 8.5 and comprises at least one inorganic ester derivative of tyrosine and/or cysteine.

Preferably the feed medium comprises at least one inorganic ester derivative of tyrosine and/or cysteine in a concentration between 10 and 50 mmol/l, preferably between 15 and 30 mmol/l.

An inorganic ester derivative according to the present invention is a product e.g. obtainable the condensation of an inorganic oxo acid and tyrosine or cysteine. Examples of inorganic oxo acids are e.g. phosphoric acid, sulfuric acid, nitric acid and boric acid. Preferred are inorganic ester derivatives derived from sulfuric acid or phosphoric acid. Inorganic ester derivatives are thus the esters of the inorganic oxo acids and cysteine or tyrosine and their salts. Examples of suitable inorganic ester derivatives of tyrosine are (S)-2-Amino-3-(4-phosphonooxy-phenyl)-propionic-acid as well as the mono-sodium salt, the di-sodium salt, the mono-potassium salt, the di-potassium salt, the calcium salt and the magnesium salt of (S)-2-Amino-3-(4-phosphonooxy-phenyl)-propionic acid.

The preferred inorganic ester derivatives can also be shown by the following formulas I and II:

with R being and X and Y being independently from one another H, Li, Na, K, ½Ca, ½Mg, preferably H, Na, K. The term propanoic acid can also be used instead of the term propionic acid.

A cell culture medium according to the present invention is any mixture of components which maintains and/or supports the in vitro growth of cells. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells as well as media supplements or feeds. In a preferred embodiment the cell culture medium is a full medium or a feed medium. A full medium also called basal medium typically has a pH between 6.8 and 7.8. A feed medium preferably has a pH below 8.5.

Typically, the cell culture media according to the invention are used to maintain and/or support the growth of cells in a bioreactor.

A feed or feed medium is a cell culture medium which is not the basal medium that supports initial growth and production in a cell culture but the medium which is added at a later stage to prevent depletion of nutrients and sustains the production phase. A feed medium can have higher concentrations of some components compared to a basal culture medium. For example, some components, such as, for example, nutrients including amino acids or carbohydrates, may be present in the feed medium at about 5×, 6×, 7×, 8×, 9×, 10×, 12×, 14×, 16×, 20×, 30×, 50×, 100×, 200×, 400×, 600×, 800×, or even about 1000× of the concentrations in a basal medium.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins to the media. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

Cells to be cultured with the media according to the present invention may be prokaryotic cells like bacterial cells or eukaryotic cells like plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the mean diameter of the particle. The particle diameter is determined by laser light scattering in silicone oil.

An inert atmosphere is generated by filling the respective container or apparatus with an inert gas. Suitable inert gases are noble gases like argon or preferably nitrogen. These inert gases are non-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media, especially the full media, according to the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are tyrosine, the proteinogenic amino acids, especially the essential amino acids, leucine, isoleucine, lysine, methionine, phenylalanine, threonine, tryptophane and valine, as well as the non-proteinogenic amino acids like D-amino acids.

Tyrosine means L- or D-tyrosine, preferably L-tyrosine.
Cysteine means L- or D-cysteine, preferably L-cysteine.
Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate ($CuSO_4.5H_2O$), Sodium Chloride (NaCl), Calcium chloride ($CaCl_2.2H_2O$), Potassium chloride (KCl), Iron(II)sulphate, sodium phosphate monobasic anhydrous ($NaH_2PO_4$), Magnesium sulphate anhydrous ($MgSO_4$), sodium phosphate dibasic anhydrous ($Na_2HPO_4$), Magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Feed media may have a different composition compared to full media. They typically comprise amino acids, trace elements and vitamins. They might also comprise saccharide components but sometimes for production reasons the saccharide components are added in a separate feed.

A suitable feed medium might for example comprise one or more of the following compounds:
L-ASPARAGINE MONOHYDRATE
L-ISOLEUCINE
L-PHENYLALANINE SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED
BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDRCHLORIDE
AMMONIUM HEPTAMOLYBDATE TETRAHYDRATE
CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

Freezing according to the present invention means cooling to a temperature below 0° C.

The gist of the present invention is to provide powdered cell culture media that can be easily dissolved in a suitable solvent by just admixing the powder and the solvent such that the powder dissolves and produces a liquid cell culture medium such as a full medium, a medium supplement, a medium subgroup or a feed with a desired and homogenous concentration of the media components.

The simple dissolving of a powdered cell culture medium is often complicated by substances like tyrosine or cysteine which have a poor solubility and/or stability in aqueous solvents. L-tyrosine for example has a solubility of 0.4 g/l in water at a temperature of 25° C. That means about 0.4 g of L-tyrosine are soluble in 1 liter of water. But the required concentration of tyrosin in cell culture media is often higher. Cysteine tends to from dimers under aerobic conditions. Those dimers are called cystine. In addition, cysteine is known to form toxic side products with metals like cupper or iron which are often present in cell culture media. Cysteine or cystine present in cell culture media can be substituted by inorganic ester derivatives according to the present invention which do not form dimers or toxic side products.

It has been found that phosphorylated and/or sulfonated derivatives of tyrosine and/or cysteine on the one hand typically have a higher solubility in aqueous solutions and on the other hand can be used as substitutes for tyrosine and/or cysteine/cystine and are equally suitable as cell culture media component as the native amino acids tyrosine and cysteine. That means that e.g. cell culture media in which L-tyrosine has been substituted by one or more inorganic ester derivatives of L-tyrosine show comparable performance in cell culture as media which comprise only L-tyrosine.

Some inorganic ester derivatives of tyrosine and cysteine are known in the art. In peptides and proteins the phosphorylation of tyrosine plays a significant role in a wide range of cellular processes and turns many protein enzymes on and off, thereby altering their function and activity.

(S)-2-Amino-3-(4-phosphonooxy-phenyl)-propionic acid mono-sodium salt has CAS number 146900-49-4. R. H. Plimmer Biochemical Journal (1941), 35, pages 461-469, discloses the synthesis of (S)-2-Amino-3-(4-phosphonooxy-phenyl)-propionic acid as well as of its 1:1-calcium salt.

The synthesis and characteristics of further new derivatives of (S)-2-Amino-3-(4-phosphonooxy-phenyl)-propionic acid, like the di-sodium salt, the di-potassium salt, the mono-potassium salt, the 2:1 calcium salt and the magnesium salts of (S)-2-Amino-3-(4-phosphonooxy-phenyl)-propionic acid, are disclosed herein.

Suitable phosphorylated derivatives of tyrosine according to the present invention are those that have been phosphorylated at the phenolic OH group, like (S)-2-Amino-3-(4-phosphonooxy-phenyl)-propionic acid or salts thereof. In an especially preferred embodiment, the phosphorylated derivative of tyrosine is a salt of (S)-2-Amino-3-(4-phosphonooxy-phenyl)-propionic acid.

Suitable sulfonated derivatives of tyrosine according to the present invention are those that have been sulfonated at the phenolic OH group, like (S)-2-Amino-3-(4-sulfonooxy-phenyl)-propionic acid or salts thereof. In an especially preferred embodiment, the sulfonated derivative of tyrosine is a salt of (S)-2-Amino-3-(4-sulfonooxy-phenyl)-propionic acid.

Suitable phosphorylated derivatives of cysteine according to the present invention are those that have been phosphorylated at the SH-group of the cysteine, like (S)-2-Amino-3-phosphonosulfanyl-propionic acid or salts thereof.

Suitable sulfonated derivatives of cysteine according to the present invention are those that have been sulfonated at the SH-group of the cysteine, like (S)-2-Amino-3-sulfosulfanyl-propionic acid or salts thereof. The synthesis of 2-Amino-3-sulfosulfanyl-propionic acid, also called (S)-2-Amino-3-sulfosulfanyl-propanoic acid, S-sulfo-cysteine or cysteine-S-sulfate, and its salts is disclosed for example in I. H. Segel and M. J. Johnson, Analytical Biochemistry 5, 330-337 and J. S. Church, D. J. Evans, Spectrochimica Acta Part A 69 (2008) 256-262. The sodium salt is further commercially available from Bachem, Switzerland.

Suitable salts are alkaline metal or alkaline earth metal salts, e.g. the lithium salts, the sodium salts, the potassium salts, the calcium salts or the magnesium salts, preferred are the sodium, potassium salts and the free acid, most preferred are the sodium salts.

In the case of inorganic ester derivatives of tyrosine, (S)-2-Amino-3-(4-phosphonooxy-phenyl)-propionic acid-di-sodium salt shows very good solubility.

Figure 1:
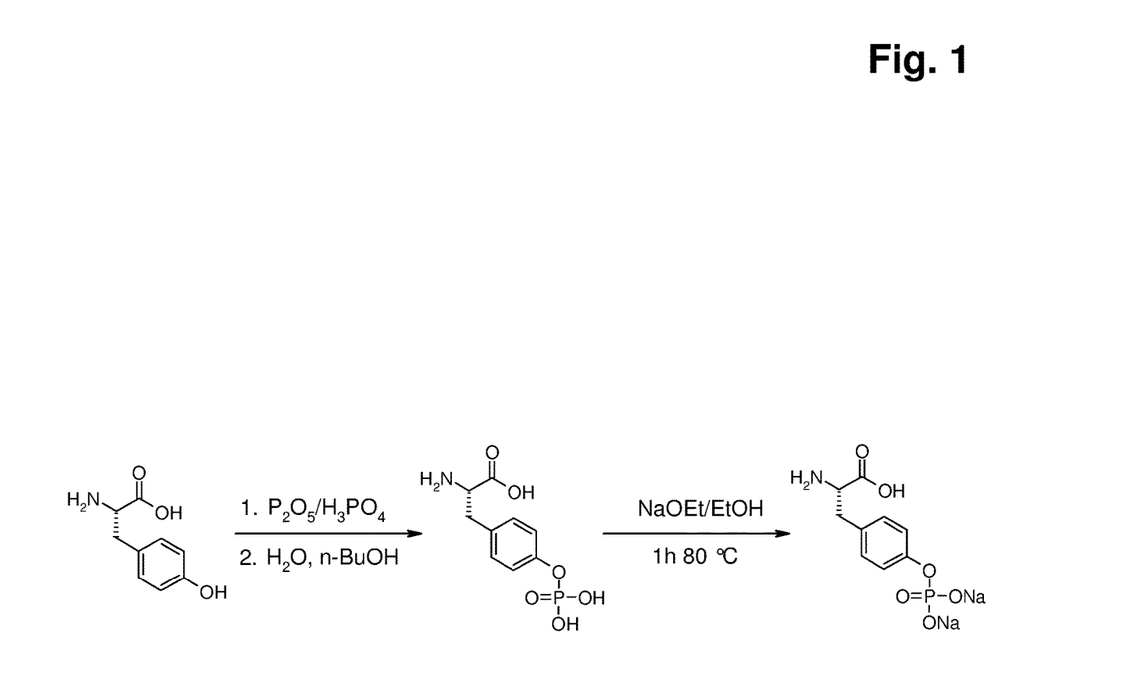
FIG. 1 shows the reaction scheme for producing (S)-2-Amino-3-(4-phosphonooxy-phenyl)-propionic-acid. Further details can be found in Example 1.

Inorganic ester derivatives of tyrosine and cysteine can be produced by any method, e.g. enzymatically or by chemical synthesis. Preferably phosphorylated derivatives of tyrosine are produced by reacting tyrosine with phosphoric acid in the presence of phosphorous pentoxide. The resulting (S)-2-Amino-3-(4-phosphonooxy-phenyl)-propionic acid can then be reacted with a suitable base like sodium hydroxide, sodium ethylate, potassium hydroxide etc. to give the relating salt. A reaction scheme of this synthesis is shown in FIG. 1.

The solubility of (S)-2-Amino-3-(4-phosphonooxy-phenyl)-propionic acid is higher than that of tyrosine (see table 1 in Example 3).

To enlarge the solubility of the tyrosine or cystein derivative even more, a salt can be formed by reacting the derivative with a suitable base as described above. The sodium salt of (S)-2-Amino-3-(4-phosphonooxy-phenyl)-propionic acid for example has a higher solubility (see table 1 in Example 3).

A cell culture medium according to the present invention can comprise one or more of the inorganic ester derivatives of tyrosine and/or cysteine, for example a mixture of the mono- and the di-sodium salt of (S)-2-Amino-3-(4-phosphonooxy-phenyl)-propionic acid.

It has been found that in case of using inorganic ester derivatives of tyrosine in full media it is favourable to add to the medium composition a small amount of tyrosine. This might due to the fact that some cells show no uptake of the inorganic ester derivatives of tyrosine. The inorganic ester derivatives of tyrosine need to be extracellularly converted to the free tyrosine by phosphatases. Typically the sufficient amount of phosphatases is available after 2 to 5 days from the starting of the cell culture.

When using inorganic ester derivatives of tyrosine in newly added feed media, that means in cell culture where the cells have already been grown for more than 2-5 days in a medium comprising tyrosine, there is no need to add tyrosine to the newly added feed medium.

Consequently, in a preferred embodiment, a full medium according to the present invention comprises at least one inorganic ester derivative of tyrosine and additionally 5 to 40% (w/w) tyrosine.

This effect is not found when using inorganic ester derivatives of cysteine. For the use of inorganic ester derivatives of cysteine the addition of cysteine is not necessary. The inorganic ester derivatives of cysteine can in any case be used as full substitute of cysteine or cystine.

In addition, unexpectedly, the inorganic ester derivatives of cysteine showed a positive effect on cell growth and productivity. Typically, cells grown with media and feed comprising inorganic ester derivatives of cysteine show an extended growth. When using inorganic ester derivatives of cysteine the viability of the cells over time is higher compared to cell cultures using cysteine.

The production of the recombinant protein is additionally increased when using inorganic ester derivatives of cysteine compared to cell culture using cysteine.

The positive effects of inorganic ester derivatives of cysteine can be obtained by using an amount equivalent to the amount of cysteine and/or cystine typically used in cell culture media.

The powdered cell culture media of the present invention are preferably produced by mixing all components and milling them. The mixing of the components is known to a person skilled in the art of producing dry powdered cell culture media by milling. Preferably, all components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 µm, most preferably between 25 and 100 µm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules.

In a preferred embodiment, the milling is performed in an inert atmosphere. Preferred inert protective gas is nitrogen.

In another preferred embodiment, all components of the mixture are freezed prior to milling. The freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The freezed mixture is then transferred from the feeder to the mill so that the mixture which is milled in the mill preferably still has a temperature below 0° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

For use of the milled powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

While media compositions comprising a higher concentration of tyrosine, e.g. 10 g/l L-tyrosine, at a pH below 8.5 would show turbidity when mixed with the solvent due to the non-dissolved tyrosine, the cell culture media according to the present invention using the same concentration of the inorganic ester derivative of tyrosine give clear solutions.

The present invention is further directed to a process for culturing cells by
a) providing a bioreactor
b) mixing the cells to be cultured with a cell culture medium according to the present invention
c) incubating the mixture of step b)

A bioreactor is any vessel or tank in which cells can be cultured. Incubation is typically done under suitable conditions like suitable temperature etc. A person skilled in the art is aware of suitable incubation conditions for supporting or maintaining the growth/culturing of cells.

It has been found that the present invention is also very suitable for the preparation of feed media. Due to the limitations in the availability of L-Tyrosine and L-Cysteine—especially in the concentrations necessary for feed media—these two molecules are typically prepared as a stock solution at basic pH 11.0-11.5. This pH has a negative impact on the overall biopharmaceutical bioproduction process. The mixing time in large scale bioreactors and the basic pH value in sum negatively affect the nutrition supply to cells and to some extent accelerate cell death by exposure to extreme basic pH values.

This results in release of intracellular proteins into the supernatant. These released proteins adhere to intact cell, which then stick to each other and form aggregates. These aggregates are destroyed by the enlarged mass inertia and the overall bioproduction process starts to skip. Lowering the tip speed is no option as these processes are anyway regulated close to oxygen supply limits.

Consequently here is a need for feed media that comprise all needed components in one feed and at high concentrations. In addition the pH of the feed should not negatively influence the cell culture.

It has been found that inorganic ester derivatives of L-tyrosine and L-Cysteine have an improved solubility and/or stability and can be used in highly concentrated feed media instead of L-tyrosine and L-cysteine respectively without any negative effect and sometimes even positive effect on the cell growth and/or productivity at a pH below 8.5.

The present invention is thus also directed to a feed medium either in form of a powdered medium or after dissolution in form of a liquid medium.

The resulting liquid medium comprises inorganic ester derivatives of tyrosine and/or cysteine in concentrations between 5 and 40 mmol/l, preferably between 10 and 30 mmol/l and preferably has a pH of 8.5 or less.

In a preferred embodiment, the pH is between 6.8 and 8.4.

The present invention is also directed to a fed batch process for culturing cells in a bioreactor by
Filling into a bioreactor cells and an aqueous cell culture medium
Incubating the cells in the bioreactor
Continuously over whole time of the incubation of the cells in the bioreactor or once or several times within said incubation time adding a cell culture medium, which is in this case a feed medium, to the bioreactor whereby the feed medium preferably has a pH of less than pH 8.5 and comprises at least one inorganic ester derivative of tyrosine and/or cysteine. Typically a feed medium comprises between 100 and 150 g/l of solid ingredients that are dissolved in the solvent.

It has been found that by using inorganic ester derivatives of tyrosine and/or cysteine a feed medium can be obtained that comprises all necessary feed components at high concentrations (overall concentration between 100 and 150 g/l). In contrast to known process where two or more different feed media need to be fed to the bioreactor, the present invention provides a medium and a method which enables the use of one feed medium that comprises all components in high concentrations. In addition the pH of the feed medium according to the present invention typically is below 8.5. Due to the limitations in the availability of L-Tyrosine and L-Cysteine in cell culture media and feed these two molecules are typically, according to state of the art, prepared as a stock solution at basic pH 11.0-11.5. This pH has a negative impact on the overall biopharmaceutical bioproduction process. The mixing time in large scale bioreactors and the basic pH value in sum negatively affect the nutrition supply to cells and to some extent accelerate cell death by exposure to extreme basic pH values. When using the inorganic ester derivative of tyrosine and/or cysteine according to the present invention, the pH of the feed medium can be kept below 8.5 while nevertheless between 10 to 13 mM the of inorganic ester derivative of tyrosine and/or cysteine are present in a feed medium with an overall concentration between 100 and 150 g/l.

Consequently, in a preferred embodiment, in the process of the present invention the feed medium that is added during the incubation either continuously or once or several times within said time to the bioreactor always has the same composition.

The present invention is further illustrated by the following figures and examples, however, without being restricted thereto.

The entire disclosure of all applications, patents, and publications cited above and below and of corresponding EP application EP 12007711.0, filed Nov. 14, 2012, are hereby incorporated by reference.

EXAMPLES

The following examples represent practical applications of the invention.

Example 1

Synthesis of (S)-2-Amino-3-(4-phosphonooxy-phenyl)-propionic-acid and its salts

(S)-2-Amino-3-(4-phosphonooxy-phenyl)-propionic-acid is synthesized according to the literature (P. F. Alewood, R. B. Johns, R. M. Valerio, *Synthesis* 1983, 30.) with subsequent conversion to its salts, starting from L-tyrosine. FIG. 1 shows the reaction scheme of the synthesis of the di-sodium salt.

Varying the stoichiometry and/or the cation of the base allows producing the single, two- or threefold charged tyrosine phosphonic acid salts or different salts respectively.

13

(S)-2-Amino-3-(4-phosphonooxy-phenyl)-propionic-acid

Structure:

Synthesis:

The reaction is carried out by dissolving 100 g (0.55 mol) L-Tyrosine in 400 g (3.48 mol) orthophosphoric acid, followed by addition of 309 g (2.13 mol) phosphorus pentoxide in five portions under cooling. The viscous solution is stirred for 20 h at 80° C., then cooled to 40° C. and hydrolyzed by addition of 400 mL water. The solution is stirred for an additional hour at 80° C. before at 60° C., 3.8 L n-butanol are added slowly. Cooling is continued to ca. 3° C. and the resulting suspension is filtered. The obtained colorless crystals are washed consecutively with water, ethanol and methyl tert-butyl ether and then dried in vacuum at 50° C.

Analytical Data:

1H-NMR (D$_2$O, 400 MHz): δ=2.94 (dd, 1H), 3.13 (dd, 1H), 3.79 (dd, 1H), 7.08-7.18 (m, 4H).

(S)-2-Amino-3-(4-phosphonooxy-phenyl)-propionic-acid mono sodium salt

Structure:

Analytical Data:

1H-NMR (D$_2$O, 400 MHz): δ=3.03 (dd, 1H), 3.21 (dd, 1H), 3.91 (dd, 1H), 7.11-7.16 (m, 2H), 7.20-7.25 (m, 2H). ICP-OES (wt-%): found 8.3%, calc. 8.1%.

14

(S)-2-Amino-3-(4-phosphonooxy-phenyl)-propionic-acid di-sodium salt

Structure:

Synthesis:

50 g (191 mmol) (S)-2-Amino-3-(4-phosphonooxy-phenyl)-propionic-acid are taken up in 146 mL (402 mmol) of a solution of NaOEt in EtOH (21 wt-%), before 12.5 mL water are added. The colourless slurry is refluxed for one hour, cooled to 0° C. and filtered. The colourless product is washed with ethanol and then dried in vacuum at 50° C.

Analytical Data:

1H-NMR (D$_2$O, 400 MHz): δ=4.18 (dd, 1H), 4.46 (dd, 1H), 5.12 (dd, 1H), 8.32-8.42 (m, 4H). ICP-OES (wt-%): found 14.1%, calc. 15.1%.

(S)-2-Amino-3-(4-phosphonooxy-phenyl)-propionic-acid mono potassium salt

Structure:

Analytical Data:

1H-NMR (D$_2$O, 400 MHz): δ=3.08 (dd, 1H), 3.29 (dd, 1H), 3.97 (dd, 1H), 7.16-7.22 (m, 2H), 7.25-7.31 (m, 2H). ICP-OES (wt-%): found 12.6%, calc. 13.1%.

(S)-2-Amino-3-(4-phosphonooxy-phenyl)-propionic-acid 2:1-calcium salt

Structure:

Analytical Data:

1H-NMR (D$_2$O, 400 MHz): δ=3.08 (dd, 1H), 3.28 (dd, 1H), 3.97 (dd, 1H), 7.16-7.22 (m, 2H), 7.25-7.31 (m, 2H). ICP-OES (wt-%): found 7.2%, calc. 7.2%.

(S)-2-Amino-3-(4-phosphonooxy-phenyl)-propionic-acid 2:1-magnesium salt

Structure:

Analytical Data:

1H-NMR (D$_2$O, 400 MHz): δ=3.07 (dd, 1H), 3.29 (dd, 1H), 3.97 (dd, 1H), 7.16-7.22 (m, 2H), 7.25-7.31 (m, 2H). ICP-OES (wt-%): found 4.3%, calc. 4.5%.

Due to spectral similarities in the $^1$H-NMR spectra between equal charged, but solvents separated tyrosine phosphate salts, ICP-OES spectrometry was carried out to unambiguously determine the corresponding cation.

Example 2

Figure 2:
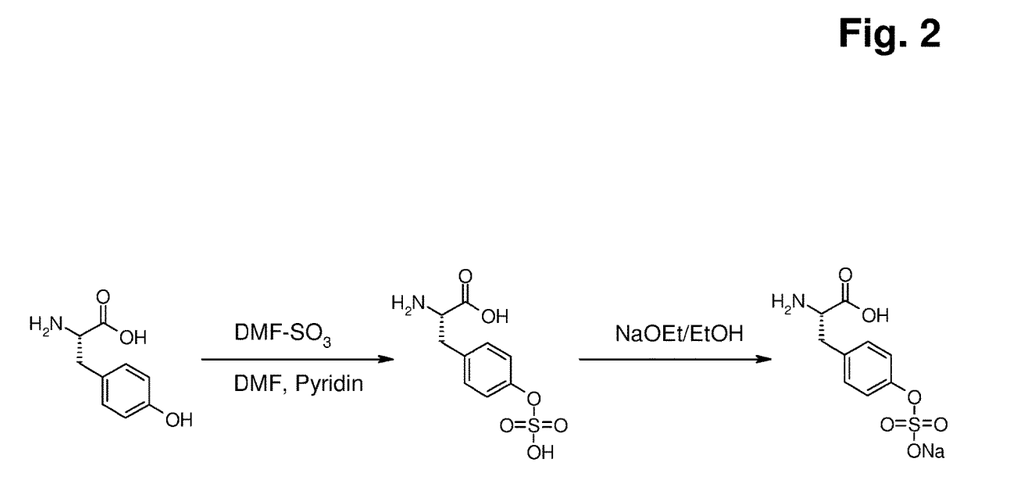
FIG. 2 shows the reaction scheme for producing (S)-2-Amino-3-(4-sulphonooxy-phenyl)-propionic-acid. Further details can be found in Example 2.

Synthesis of (S)-2-Amino-3-(4-sulphonooxy-phenyl)-propionic-acid and its salts (S)-2-Amino-3-(4-sulphonooxy-phenyl)-propionic-acid can be synthesized according to the literature (* S. Futaki, T. Taike, T. Yagami, T. Ogawa, T. Akita, K. Kitagawa, *J: Chem. Soc. Perkin Trans./*1990, 1739.) with possible subsequent conversion to its salts, starting from L-tyrosine. FIG. 2 shows the reaction scheme of the synthesis of the sodium salt.

Varying the stoichiometry and/or the cation of the base allows producing the single or two-fold charged tyrosine sulphonic acid salts or different salts respectively.

Example 3

Solubility in Water

The solubility of L-Tyrosine (compound D1), (S)-2-Amino-3-(4-phosphonooxy-phenyl)-propionic acid (compound D2), (S)-2-Amino-3-(4-phosphonooxy-phenyl)-propionic acid sodium salt (compound D3) and (S)-2-Amino-3-(4-phosphonooxy-phenyl)-propionic acid di-sodium salt (compound D4) in water is tested at 20, 25 and 30° C. Table 1 shows the results.

| compound | solubility at 20° C. | solubility at 25° C. | solubility at 30° C. |
| --- | --- | --- | --- |
| D1 | 0.03% | 0.04% | 0.04% |
| D2 | 0.7% | 1.0% | 0.8% |
| D3 | 5.5% | 5.3% | 11.4% |
| D4 | 9.8% | 10.1% | 9.2% |

Example 4

Solubility in Complex Cell Culture Medium

Dulbecco's Modified Eagle Medium, also known as DMEM, is a medium often used for growing animal cells. The ingredients of DMEM are in mg/l:

Inorganic Salts:
CaCl$_2$ (anhydrous): 200.00
Fe(NO$_3$).9H$_2$O: 0.10
KCl: 400.00
MgSO$_4$ (anhydrous): 97.67
NaCl: 6400.00
NaH$_2$PO$_4$.H$_2$O: 125.00
Other Components:
D-Glucose: 4500.00
Sodium pyruvate: 110.00
Pluronic 1000.00
Hepes 15 mM
Amino Acids:
L-Arginin.HCl: 84.00
L-Cystine.2HCl: 63.00
L-Glutamine: 584.00
Glycine: 30.00
L-Histidine HCl H$_2$O: 42.00
L-Isoleucin: 105.00
L-Leucine: 105.00
L-Lysin HCl: 146.00
L-Methionine: 30.00
L-Phenylalanine: 66.00
L-Serine: 42.00
L-Threonine: 95.00
L-Tryptophane: 16.00
L-Tyrosine 2Na.2H$_2$O: 248.00
L-Valine: 94.00
Vitamins:
D-Calciumpantothenate: 4.00
Cholin chloride: 4.00
Folic acid: 4.00
i-Inositol: 7.20
Niacinamide: 4.00
Riboflavine: 0.40
Thiamine.HCl: 4.00

The same media composition is made but L-Tyrosine 2Na.2H$_2$O is substituted by (S)-2-Amino-3-(4-phosphonooxy-phenyl)-propionic acid di sodium salt in the equivalent molar ratio.

For both media compositions, all ingredients are mixed and milled according to the method of the present invention comprising a dosage snail and a pin mill.

The resulting powdered cell culture medium is dissolved in deionized water at 25° C. The solubility is measured after 10 minutes of mixing (in a flask with a stirrer) While the media composition with the phosphorylated tyrosine derivative is a clear solution, the composition comprising L-tyrosine is not clear but shows turbidity.

Cell Culture Experiments

Example 5

Figure 3:
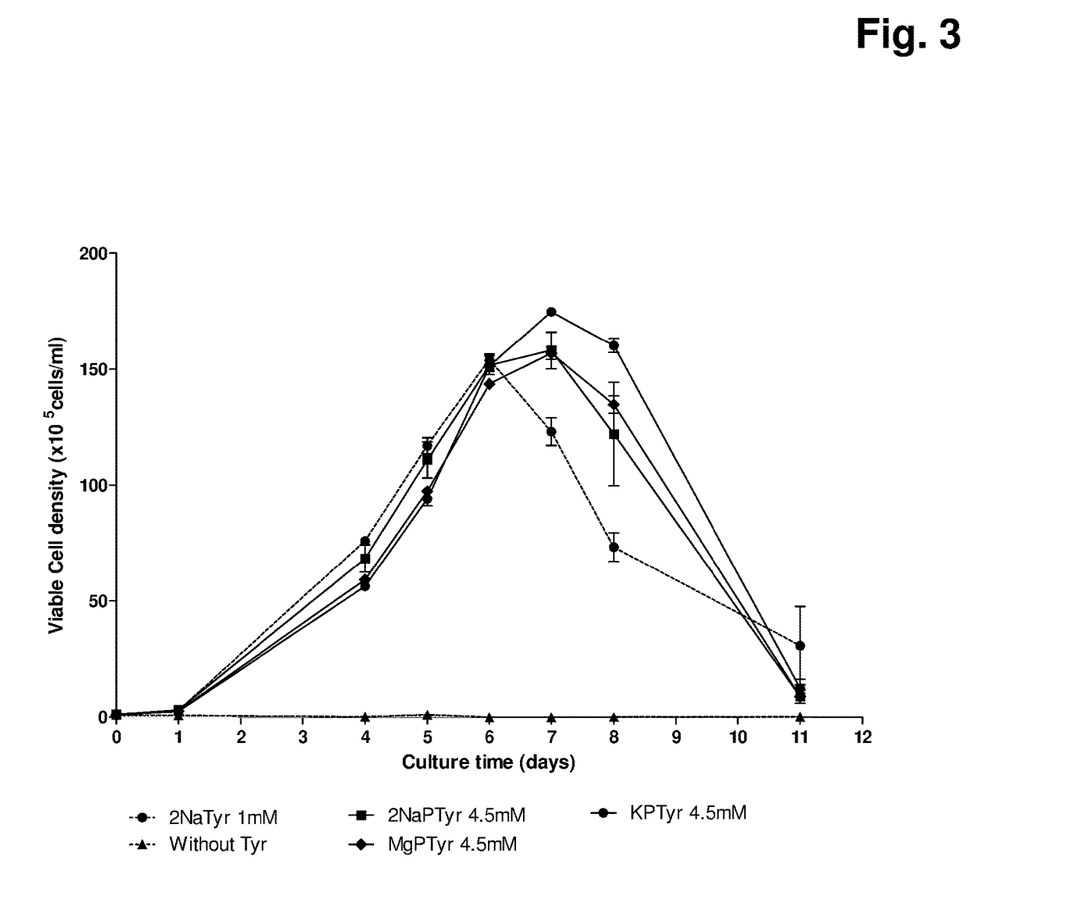
FIGS. 3 and 4 show cell growth experiments in batch using a cell culture medium according to the present invention. Further details can be found in Example 5 and 6.

The data for this experiment are shown in FIG. 3. Batch experiment in chemically defined medium where tyrosine was replaced by PTyr salts. PTyr means (S)-2-Amino-3-(4-phosphonooxy-phenyl)-propionic-acid salt. If the concentration of PTyr used was the same as the concentration of Tyrosine in the medium, cells didn't grow (not shown). If dissolved at a concentration of 4.5 mM in the CDM (versus 1 mM in the control), cells could grow, showing an even higher maximum viable cell density as in the control and overall an extended growth (2 days). Later analysis indicated that the initial growth was possible through the free tyrosine coming from the PTyr derivate synthesis (synthesis impurity 5% (w/w)). The extended growth could be attributed to the direct effect of PTyr after its metabolic cleavage in free tyrosine and phosphate Example 6

Figure 4:
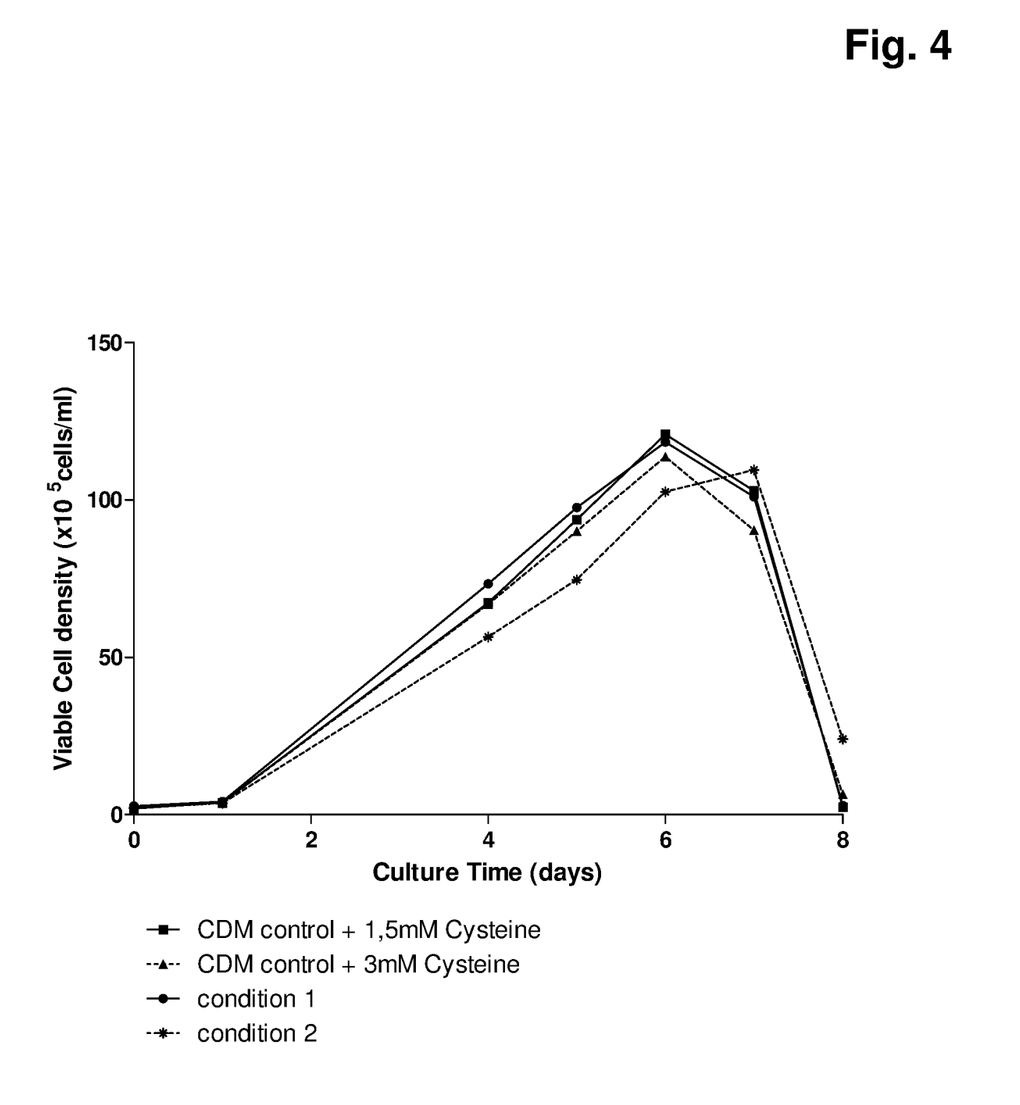

The data for this experiment are shown in FIG. 4. Batch experiment in chemically defined medium where Cysteine was replaced by S-sulfocysteine sodium salt (equivalent concentration). The CDM powder used as basis was depleted in Cysteine and Cystine and supplemented during reconstitution with Cysteine for the control conditions (1.5 and 3 mM) or with S-sulfocysteine sodium salt for the test conditions (1.5 and 3 mM). Cells showed a comparable growth if cultured in chemically defined medium containing Cysteine or S-sulfocysteine sodium salt showing that S-sulfocysteine sodium salt can be used as replacement of cysteine.

Example 7

Figure 5:
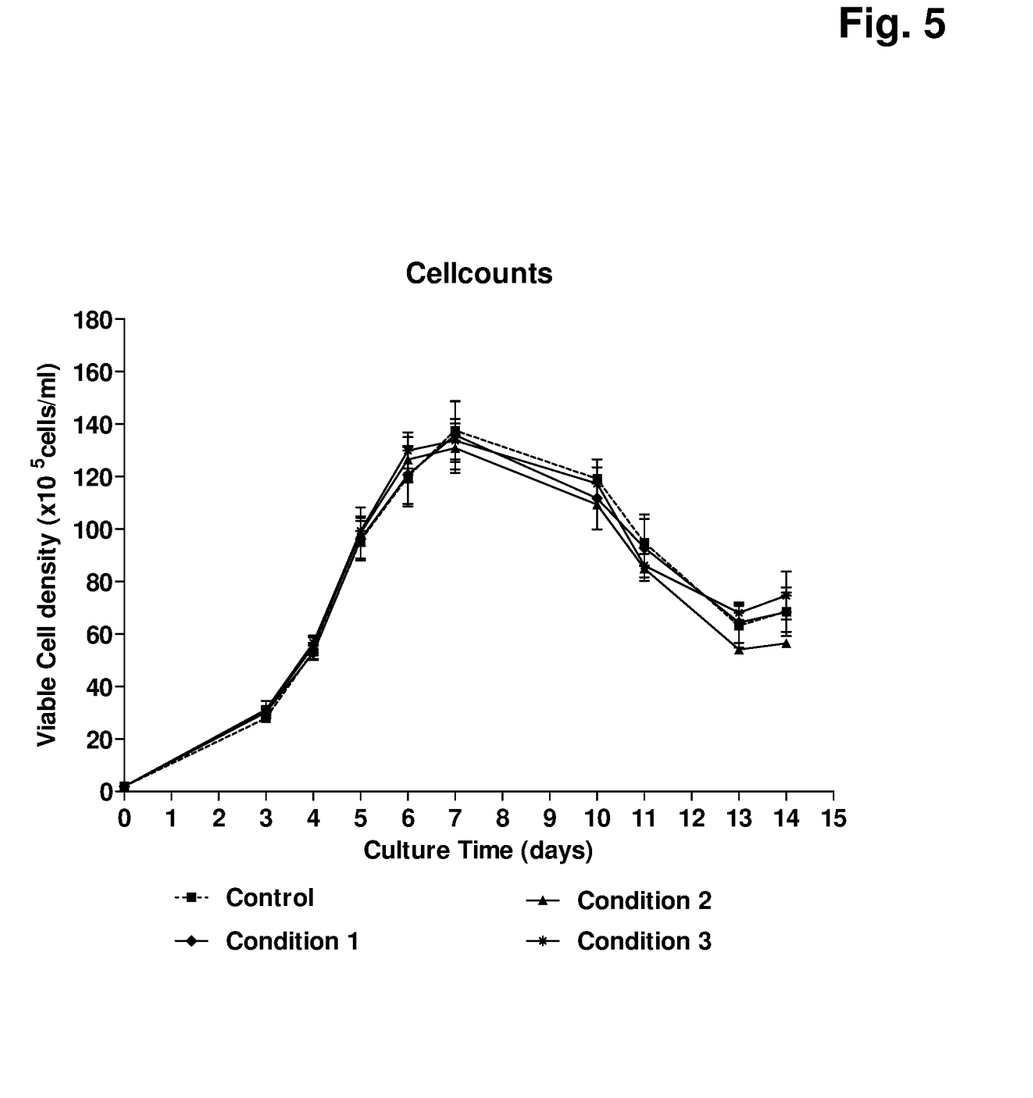
FIGS. 5 and 6 show the results of a fedbatch cell culture experiment in which the optimized fed-batch according to the invention with (S)-2-Amino-3-(4-sulphonooxy-phenyl)-propionic-acid salts are used. Details can be found in Example 7.
Figure 6:
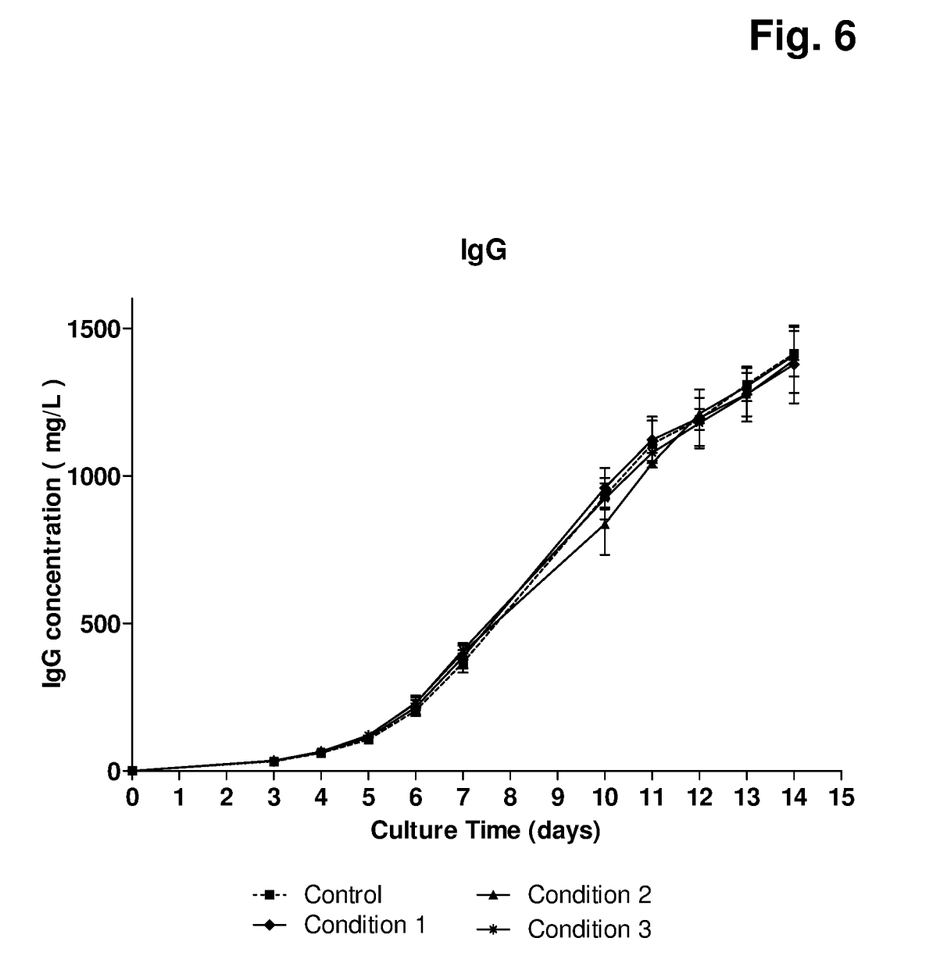

FIGS. 5 and 6 show the viable cell density and IgG concentration over time in a fed batch process. Recombinant CHO cells are grown in fully chemically defined basal media and a feed containing phospho-Tyr salts at pH 7.0 is added on day 3; 5, 7 and 9 (addition of % v/v of 3%; 6% 6% 6%). Condition 1 corresponds to PTyr di sodium salt, Condition 2 corresponds to PTyr Potassium salt and condition 3 corresponds to PTyr Magnesium salt solubilized at a concentration of 30 mM in the neutral pH feed. In these cases, Cysteine is still added as a separate feed at pH 11.

The process is performed in 30 mL spin tubes at 37° C., 5% CO$_2$, agitation 320 rpm. For control, according to the state of the art, tyrosine 2Na+ and Cysteine are solubilized at pH 11 in a separate feed and added at day 3; 5; 7; 9 in % (V/V) of 0.3%, 0.6%, 0.6% and 0.6%. Consequently, the main feed does not contain any Cysteine and tyrosine and is added like described above.

The glucose concentration is measured every day and adjusted accordingly to maintain a concentration >2 g/L It can be seen that the 3 phosphoTyr salts (sodium, potassium, magnesium) can be used in highly concentrated neutral feeds in fed-batch processes with no negative impact on either growth or titer, thus simplifying the overall process

Example 8

Figure 7:
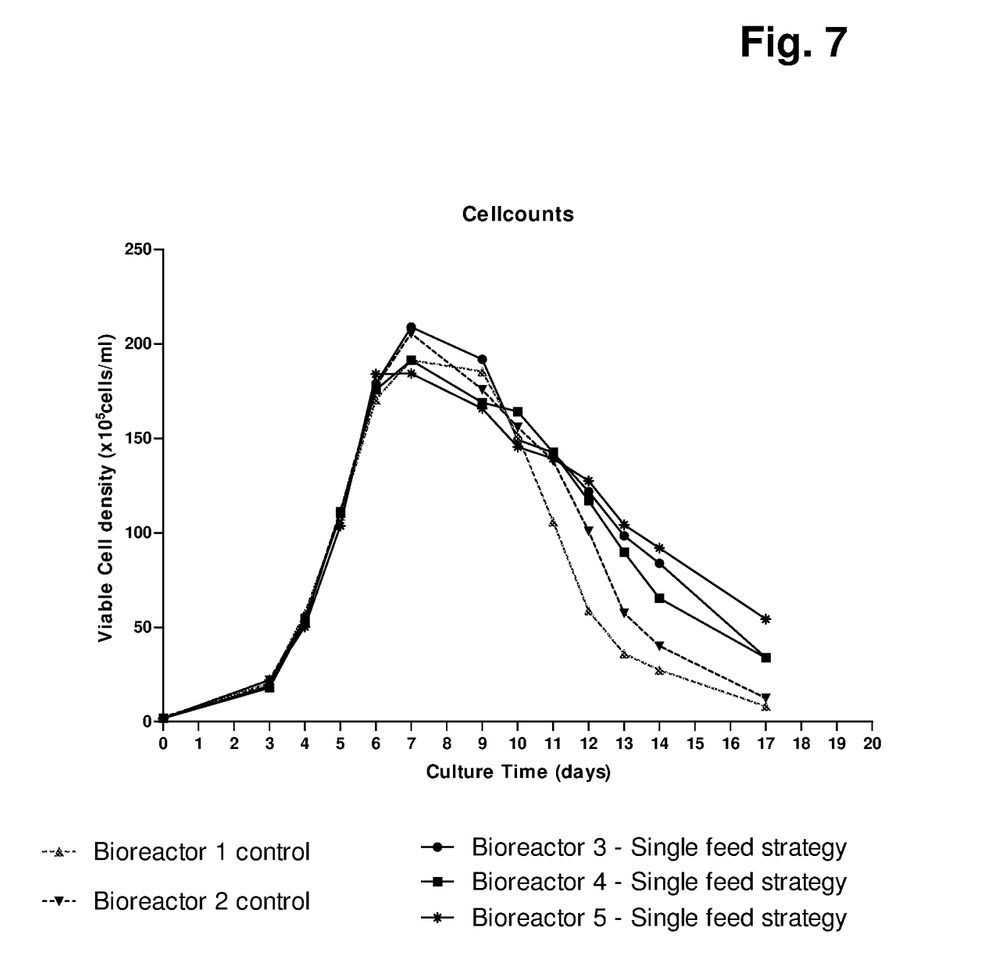
FIGS. 7 and 8 show the results of a fedbatch cell culture experiment in which the optimized fed-batch according to the invention with (S)-2-Amino-3-(4-sulphonooxy-phenyl)-propionic-acid salts and (S)-2-Amino-3-sulfosulfanyl-propionic acid sodium salt are used. Details can be found in Example 8.
Figure 8:
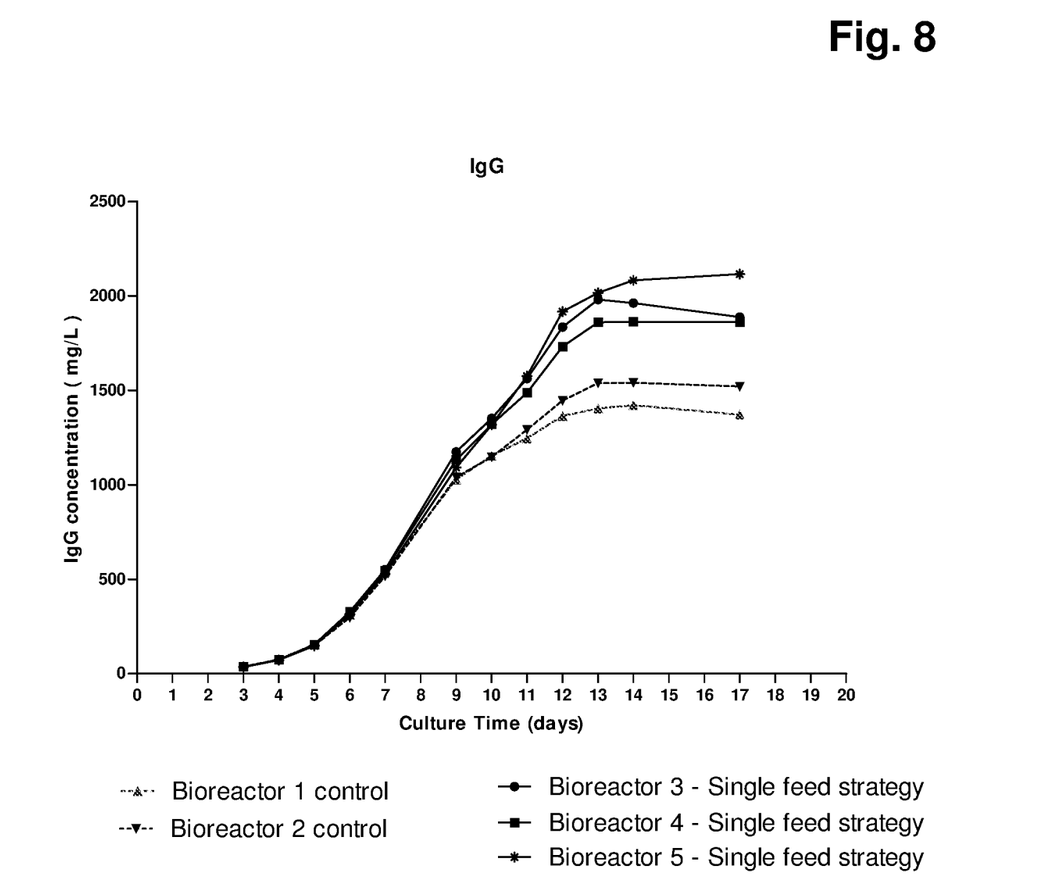

FIGS. 7 and 8 show the viable cell density and IgG concentration over time in a fed batch process. Recombinant CHO cells are grown in fully chemically defined basal media and a feed containing both S-sulfocysteine and PTyr 2Na+ at pH 7.0. Feed is added on day 3; 5, 7, 9 and 14 (addition of % v/v of 3%; 6% 6% 6%, 3%). The process is performed in 1.2 L bioreactors at 37° C., pH 7.0, 50% dissolved oxygen, agitation 140 rpm. For control, according to the state of the art, tyrosine 2Na+ and Cysteine are solubilized at pH 11 in a separate feed and added at day 3; 5; 7; 9, 14 in % (V/V) of 0.3%, 0.6%, 0.6%, 0.6%, 0.3%. The glucose concentration is measured every day and adjusted accordingly to maintain a concentration >2 g/L It can be seen that the use of S-sulfocysteine in the main feed (here in combination with PTyr 2Na+) induces an extended growth in comparison to the control and shows a significant increase in titer.

The invention claimed is:

1. A process for culturing mammalian cells by
   a) providing a bioreactor
   b) mixing the mammalian cells to be cultured with a cell culture medium comprising a compound of formula I:

with R being phosphonate or sulphonate or a salt thereof
   c) incubating the mixture of step b).

2. A fed batch process for culturing mammalian cells in a bioreactor comprising
   (i) adding mammalian cells and an aqueous cell culture medium into a bioreactor,
   (ii) incubating the mammalian cells in the bioreactor and
   (iii) feeding a cell culture feed medium continuously over the whole time of the incubation of the mammalian cells in the bioreactor or once or several times within said incubation time, to the bioreactor
   whereby the feed medium has a pH of less than pH 8.5 and comprises at least one phosphate or sulphate ester derivative of cysteine where the ester occurs at the thiol moiety of the cysteine.

3. The fed-batch process according to claim 2 wherein the feed medium comprises the at least one phosphate or sulphate ester derivative of cysteine in a concentration between 10 and 30 mmol/l.

4. The fed-batch process according to claim 2, wherein the at least one phosphate or sulphate ester derivative of cysteine is represented by the structure of formula I:

where R is or and X and Y being independently from one another H, $Li^+$, $Na^+$, $K^+$, $½Ca^{2+}$ and $½Mg^{2+}$.

5. The fed-batch process according to claim 2, wherein the at least one phosphate or sulphate ester derivative of cysteine is (S)-2-amino-3-sulfosulfanylpropanoic acid sodium salt.

6. The fed-batch process according to claim 2, wherein the feed medium further comprises (S)-2-Amino-3-(4-sulphonooxy-phenyl)-propionic acid salt.

7. The fed-batch process according to claim 2, wherein the pH of the feed medium is between 6.5 and 8.5.

8. The fed-batch process according to claim 7, wherein the pH of the feed medium is between 6.8 and 7.8.

9. The fed batch process according to claim 4, wherein X is H, $Na^+$ or $K^+$.

10. The fed batch process according to claim 4, wherein Y is H, $Na^+$ or $K^+$.

* * * * *

UNITED STATES PATENT AND TRADEMARK OFFICE
CERTIFICATE OF CORRECTION

PATENT NO. : 10,619,131 B2
APPLICATION NO. : 15/952874
DATED : April 14, 2020
INVENTOR(S) : Joerg Von Hagen et al.

Page 1 of 1

It is certified that error appears in the above-identified patent and that said Letters Patent is hereby corrected as shown below:

In the Claims

Column 18, Line 46 (Claim 1), reads as follows:
-- with R being phosphonate or sulphonate or a salt thereof --

Should read:
-- with R being phosphate or sulphate or a salt thereof --.

Signed and Sealed this
Twenty-third Day of June, 2020

Andrei Iancu
*Director of the United States Patent and Trademark Office*